United States Patent
Cybulski et al.

(10) Patent No.: US 6,595,316 B2
(45) Date of Patent: Jul. 22, 2003

(54) TENSION-ADJUSTABLE MECHANISM FOR STETHOSCOPE EARPIECES

(75) Inventors: George Cybulski, Beaconsfield (CA); Larrimore Adams, Lachine (CA); Victor F. Lanzo, Laval (CA)

(73) Assignee: Andromed, Inc., St.-Laurent (CA)

(*) Notice: Subject to any disclaimer, the term of this patent is extended or adjusted under 35 U.S.C. 154(b) by 6 days.

(21) Appl. No.: 09/907,796

(22) Filed: Jul. 18, 2001

(65) Prior Publication Data

US 2003/0015368 A1 Jan. 23, 2003

(51) Int. Cl.[7] .............................. A61B 7/02; A61B 7/04
(52) U.S. Cl. ........................ 181/131; 381/67; 381/379
(58) Field of Search ............................. 181/128–132, 181/135, 137; 379/430; 381/67, 380, 379, 376, 382, 374, 309; 2/209; 128/866, 864

(56) References Cited

U.S. PATENT DOCUMENTS

| | | | | |
|---|---|---|---|---|
| 3,630,308 A | * | 12/1971 | Ravin .......................... | 181/131 |
| 3,746,124 A | * | 7/1973 | Wilson et al. .............. | 181/131 |
| 4,149,610 A | * | 4/1979 | Saiya et al. .................. | 181/131 |
| 4,277,654 A | * | 7/1981 | Penning ....................... | 381/309 |
| 4,406,346 A | * | 9/1983 | Pope, Jr. ..................... | 181/131 |
| 4,783,822 A | | 11/1988 | Toole et al. ................. | 381/379 |
| 5,561,275 A | | 10/1996 | Savage et al. .............. | 181/131 |
| 5,862,241 A | | 1/1999 | Nelson ........................ | 381/379 |

* cited by examiner

Primary Examiner—Robert E. Nappi
Assistant Examiner—David Warren
(74) Attorney, Agent, or Firm—Fay Kaplun & Marcin LLP

(57) ABSTRACT

A tension-adjusting mechanism for the elongated earpieces of a stethoscope comprises a neckpiece and, for each earpiece, a pivot mechanism portion between the proximal end of the earpiece and the neckpiece, a spring mechanism portion between the proximal end of the earpiece and the neckpiece, and a tension-adjusting mechanism portion between the spring member and the neckpiece. For each earpiece, the pivot mechanism portion defines a pivot axis about which the earpiece pivots, and the spring mechanism portion comprises a resilient blade deforming upon spreading apart of the earpieces. This deformation produces a tension on the earpieces opposing to further spreading apart thereof. The tension-adjusting mechanism portion defines a plurality of interchangeable point of contacts with the resilient blades, which contact points having different positions relative to the neckpiece.

23 Claims, 5 Drawing Sheets

TENSION-ADJUSTABLE MECHANISM FOR STETHOSCOPE EARPIECES

BACKGROUND OF THE INVENTION

1. Field of the Invention

The present invention relates to a tension-adjustable mechanism for the earpieces of a stethoscope. The present invention also relates to a stethoscope headset comprising this mechanism.

2. Brief Description of the Prior Art

A tension-adjustable mechanism for the earpieces of a stethoscope has been proposed in the following prior art patent:

U.S. Pat. No. 5,561,275 (Savage et al.) Oct. 1, 1996

According to this prior art mechanism, the two earpieces comprise respective weakened proximal end portions inserted side by side in a longitudinally movable sleeve. Longitudinal movement of the sleeve on the weakened end portions of the earpieces change the amplitude of the tension on the earpieces when these earpieces are spread apart from each other.

Although this prior art tension-adjusting mechanism is efficient, further adjustment capability is often required to meet with the requirements, needs and/or preferences of a wide range of users.

Therefore, need exists for a more versatile tension-adjusting mechanism capable of fulfilling the requirements, needs and/or preferences of a wide range of users.

SUMMARY OF THE INVENTION

In accordance with the present invention, there is provided a tension-adjusting mechanism for an elongated stethoscope earpiece having a proximal end. This tension-adjusting mechanism comprises a stethoscope neckpiece, a pivot mechanism portion, a spring mechanism portion, and a tension-adjusting mechanism portion. The pivot mechanism portion is interposed between the proximal end of the earpiece and the neckpiece, and defines a pivot axis about which the earpiece pivots relative to the neckpiece. The spring mechanism portion is interposed between the proximal end of the earpiece and the neckpiece, and comprises a spring member which deforms upon pivoting of the earpiece about the neckpiece in an outward direction. Deformation of the spring member produces a tension on the earpiece opposing to further pivoting of the earpiece in the outward direction. Regarding the tension-adjusting mechanism portion, it is interposed between the spring member and the neckpiece and defines a plurality of interchangeable point of contacts with the spring member. These points of contacts with the spring member have different positions relative to the neckpiece.

The above mentioned pivot mechanism portion, spring mechanism portion, and tension-adjusting mechanism portion provide for the level of versatility required to fulfill the requirements, needs and/or preferences of a wide range of users.

Preferably, the pivot mechanism portion comprises abutment surfaces restricting, by abutment, free pivotal movement of the earpiece about the neckpiece within given limits.

According to other preferred embodiments of the tension-adjusting mechanism:

the pivot mechanism portion comprises a pivot pin pivotally mounted on the neckpiece, and a pivot tube pivotally mounted on the pivot pin and connected to the proximal end of the earpiece;

the spring member comprises a resilient blade having one end formed with the pivot pin;

the pivot tube has an open, axial slot through which the resilient blade extends when the pivot pin is inserted in that pivot tube, the resilient blade has a thickness, and the slot has a width larger than the thickness of the blade to allow limited pivotal movement of the pivot tube about the pivot pin; and the pivot tube has an annular end face provided with a lug, the neckpiece has a pair of abutment surfaces situated on opposite sides of the lug, and the lug abuts on either abutment surface to restrict pivotal movement of the pivot tube about the neckpiece within predetermined limits.

The present invention further relates to a headset for electronic stethoscope, comprising first and second elongated stethoscope earpieces each having a proximal end, and the above described tension-adjusting mechanism for each elongated stethoscope earpiece.

Preferably, the stethoscope neckpiece is common to both the first and second elongated stethoscope earpieces, the neckpiece comprises a hollow shell formed with openings for the proximal ends of the earpieces, and the hollow shell comprises a front shell portion and a rear shell portion assembled together to form that hollow shell.

In accordance with a preferred embodiment:

the resilient blade associated to the first earpiece has a first distal end section opposite to the pivot pin;

the resilient blade associated to the second earpiece has a second distal end section opposite to the pivot pin;

the tension-adjusting mechanism portion associated to both the first and second earpieces comprises a tension-adjusting cam having a geometrical axis, rotatable about this geometrical axis and lockable in either first, second and third angular positions;

the tension-adjusting cam comprises an axial member having an outer tubular surface and two first points of contact with the first and second distal end sections, respectively, formed by two points of this outer tubular surface, respectively, when the tension-adjusting cam is locked in the first angular position;

the axial member of the tension-adjusting cam comprises, on its outer tubular surface, first and second diametrically opposite, axial and radial fins of intermediate height having respective first and second free axial edge surfaces, and two second points of contact with the first and second distal end sections, respectively, formed by these first and second free axial edge surfaces of the first fin, respectively, when the tension-adjusting cam is locked in the second angular position;

the axial member of the tension-adjusting cam comprises, on its outer tubular surface, third and fourth geometically opposite, axial and radial fins of larger height with third and fourth free axial edge surfaces, respectively, and two third points of contact with the first and second distal end sections, respectively, formed by these third and fourth free axial edge surfaces of the second fin, respectively, when the tension-adjusting cam is locked in the third angular position;

the neckpiece comprises a hole with peripheral notches, and the tension-adjusting cam comprises lugs engaging the peripheral notches of the hole in the neckpiece to lock the tension-adjusting cam in either the first, second and third angular positions; and the tension-adjusting mechanism associated to both the first and second earpieces comprises a spring element interposed between the neckpiece and the tension-adjusting cam and spring biasing the lugs of this tension-adjusting cam in the notches of the hole in the neckpiece, whereby, to be rotated, the tension-adjusting cam is moved against the spring-biasing force produced by the spring element to disengage the lugs from the notches and is rotated and then released to engage the lugs with other notches.

The foregoing and other objects, advantages and features of the present invention will become more apparent upon reading of the following non-restrictive description of a preferred embodiment thereof, given for the purpose of illustration only with reference to the accompanying drawings.

DETAILED DESCRIPTION OF THE PREFERRED EMBODIMENT

Figure 1:
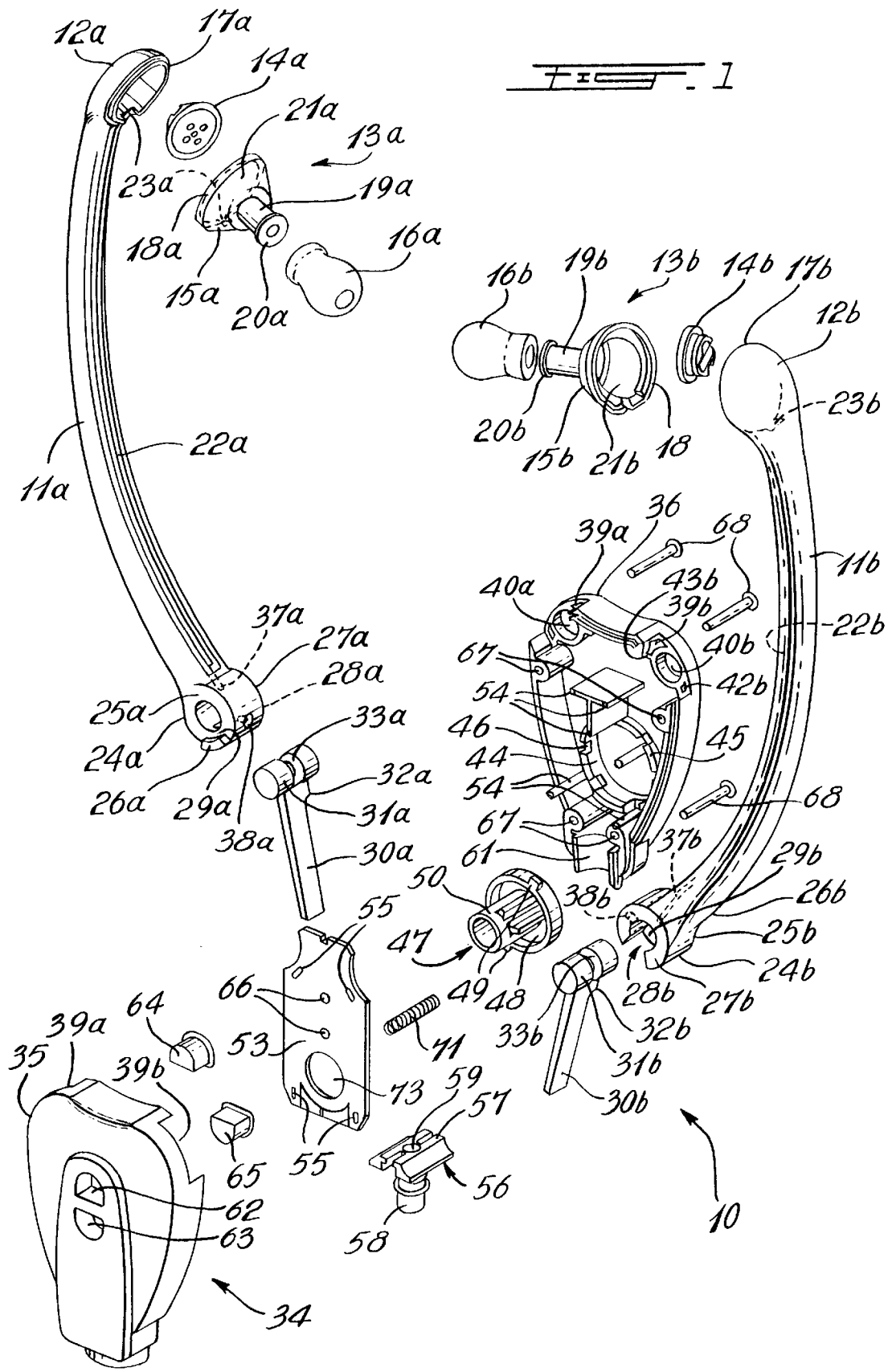
FIG. 1 is an exploded view of a headset for electronic stethoscope in accordance with the present invention.

Preferred embodiments of the tension-adjustable mechanism for an elongated stethoscope earpiece and headset for electronic stethoscope according to the present invention will now be described with reference to the appended drawings. Just a word to mention that the present invention equally apply to non electronic stethoscopes.

In the appended drawings, the tension-adjustable headset for electronic stethoscope is generally identified by the reference 10.

The headset 10 comprises two earpieces 11a and 11b. Since these two earpieces 11a and 11b and the associated mechanisms are identical but symmetrical, they will be described concurrently. In the appended figures, the references related to the earpiece 11a bear the indicia "a" while the references related to the earpiece 11b bear the indicia "b".

The earpiece 11a,11b is constituted by an elongated, arched member advantageously made of slightly flexible plastic material.

The earpiece 11a,11b comprises a distal cup-shaped end 12a,12b to receive an earphone assembly 13a,13b. The earphone assembly 13a,13b comprises a speaker 14a,14b, a speaker housing 15a,15b and an eartip 16a,16b.

The distal cup-shaped end 12a,12b comprises an inner shouldered rim 17a,17b. In the same manner, the speaker housing 15a,15b comprises a proximal cup-shaped portion 21a,21b with an outer shouldered rim 18a,18b. The shouldered rims 17a,17b and 18a,18b are configured to mate each other. The speaker housing 15a,15b finally comprises an axial, distal tube 19a,19b with a distal, externally protruding rim 20a,20b.

To assemble the earphone assembly 13a,13b, the speaker 14a,14b is first placed in the cup-shaped end 12a,12b of the earpiece 11a,11b. The shouldered rim 18a,18b of the speaker housing 15a,15b is then glued or otherwise secured to the shouldered rim 17a,17b of the cup-shaped end 12a,12b. The cup-shaped end 12a,12b and portion 21a,21b then define a cavity in which the speaker 14a,14b snugly fits. Finally, the eartip 16a,16b is placed on the tube 19a,19b. Of course, the eartip 16a,16b is tubular and has an inner configuration adapted to fit on the tube 19a,19b. Those of ordinary skill in the art will appreciate that the distal, externally protruding rim 20a,20b will hold the eartip 16a,16b on the tube 19a,19b.

Just a word to mention that the eartip 16a,16b is made of soft, resilient material such as foam, for ensuring comfort of the user's ear.

The earpiece 11a,11b has a longitudinal channel 22a, 22b on the inner face of that earpiece 11a,11b. Also, the shouldered rims 17a,17b and 18a,18b are structured to form an opening (see 23a,23b) through which the channel 22a,22b communicates with the cavity defined by the cup-shaped end 12a,12b and portion 21a,21b when secured to each other. This opening 23a,23b and the channel 22a,22b define a passage for electrical wires connected to the speaker 14a, 14b along the earpiece 11a,11b.

Pivot Mechanism Portion

The proximal end of the earpiece 11a,11b is provided with an integral, transversally extending pivot tube 24a,24b. Therefore, the earpiece 11a,11b and the pivot tube 24a,24b are made of a single piece of plastic material. On a first side, the pivot tube 24a,24b includes an annular flat face 25a,25b with a semicircular lug 26a,26b. On the second side, the pivot tube 24a,24b has also an annular face 27a,27b from which an open, axial slot 28a,28b extends. In the preferred embodiment, the position and width of the slot 28a,28b corresponds to the position and length of the semicircular lug 26a,26b. A relatively thin wall 29a,29b is left between the inner end of the slot 28a,28b and the annular face 25a,25b.

A spring blade 30a,30b will now be described. This spring blade 30a,30b is made of molded and resilient plastic material and has at the proximal end thereof an integral, proximal and transversally extending cylindrical pivot pin 31a,31b. Accordingly, the spring blade 30a,30b and the pivot pin 31a,31b are made of a single piece of plastic material. The spring blade 30a,30b has a constant width but a thickness which gradually thins from the pivot pin 31a,31b to the distal end of that blade. The blade 30a,30b further comprises a lateral extension 32a,32b adjacent to the pivot pin 31a,31b. Finally, the pivot pin 31a,31b has a semicircular groove 33a,33b.

Figure 2:
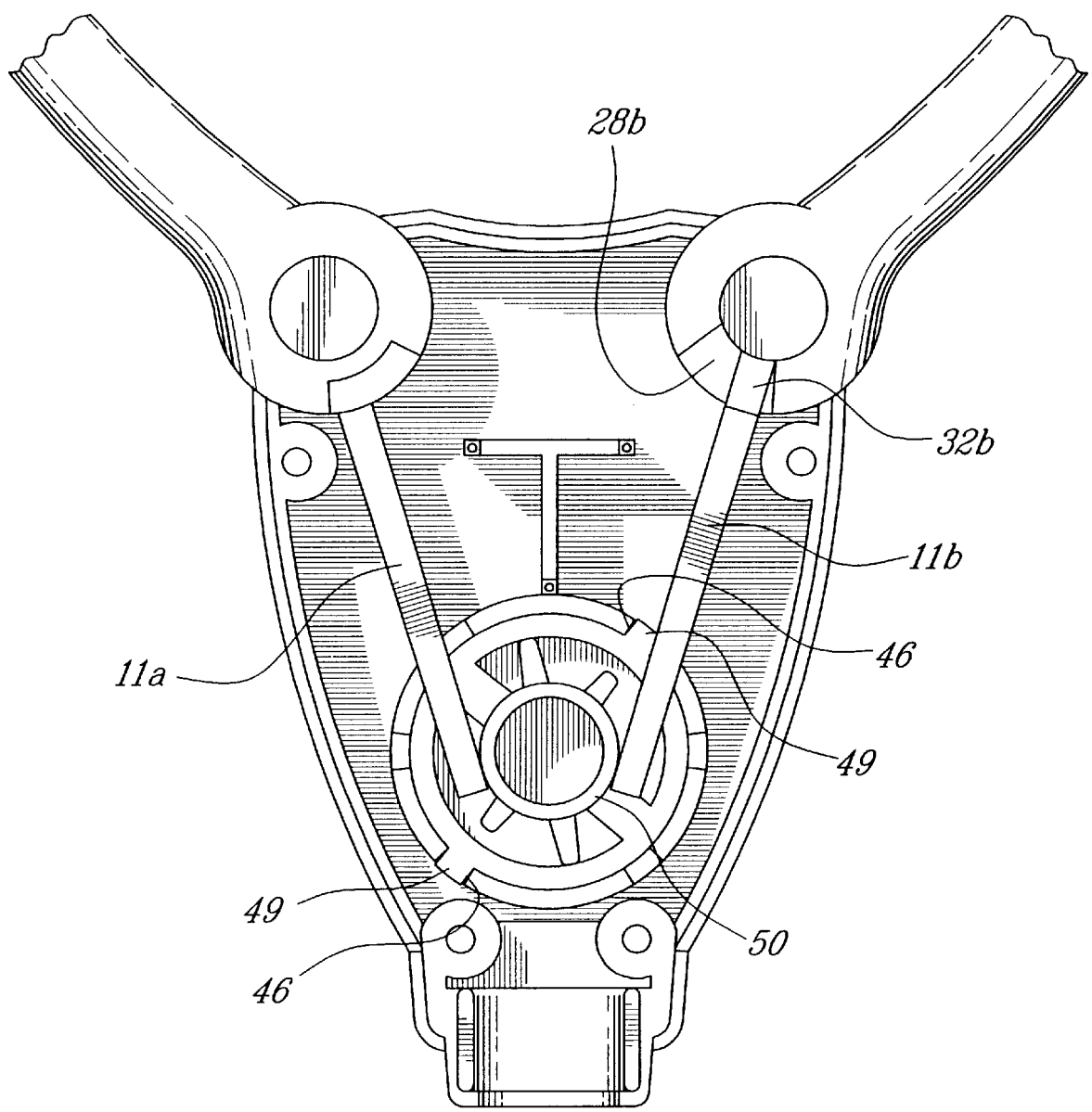
FIG. 2 is a first inner elevation view of a rear shell portion of a neckpiece of the headset of FIG. 1, showing a tension-adjusting cam in a first angular position.

The pivot pin 31a,31b is inserted in the pivot tube 24a,24b, with the blade 30a,30b including the lateral extension 32a,32b extending through the slot 28a,28b. As can be seen in FIG. 2, the width of the blade 30a,30b and lateral extension 32a,32b is equal to the length of the slot 28a,28b. Also, the width of the slot 28a,28b is larger that the thickness of the blade 30a,30b whereby free pivotal movement of the pivot tube 24a,24b about the pivot pin 31a,31b is allowed within predetermined limits.

The electrical wires connected the speaker 14a,14b and running through the channel 22a,22b leave the channel 22a,22b at the proximal end of the earpiece 11a,11b through a first hole 37a,37b in the pivot tube 24a,24b, the semicircular groove 33a,33b in the pivot pin 31a,31b, and a hole 38a,38b in the pivot tube 24a,24b to thereby reach the inside of a shell 35,36 of a neckpiece 34, common to the two earpieces 11a and 11b.

The headset 10 comprises the stethoscope neckpiece 34 of which the shell 35,36 comprises a rear triangular shell portion 35 and a front triangular shell portion 36. When assembled together, the triangular shell portions 35 and 36 define an opening 39a,39b at an upper corner thereof and through which the proximal end of the earpiece 11a,11b and the pivot tube 24a,24b extend. In the proximity of the opening 39a,39b, the shell portion 36 comprises an inner cylindrical blind hole 40a,40b to receive a first end of the pivot pin 31a,31b. In the same manner, the shell portion 35 comprises an inner cylindrical blind hole 41a,41b (FIG. 3) coaxial with blind hole 40a,40b and receiving the second end of pivot pin 31a,31b. Accordingly, when shell portion 35 is assembled to shell portion 36, the pivot pin 31a,31b is free to pivot in the blind holes 40a,40b and 41a,41b. Pivotal movement of the pivot pin 31a,31b in the coaxial blind holes 40a,40b and 41a,41b is restricted within a given angle, that is within predetermined limits by the semicircular lug 26a, 26b which abuts on faces 42a,42b and 43a,43b situated on opposite sides of the lug 26a,26b.

It should be pointed out here that the pivot pin 31a,31b, the pivot tube 24a,24b, and the cylindrical blind holes 40a,40b and 41a,41b define a pivot axis about which the earpiece 11a,11b pivots relative to the neckpiece 34.

Tension-Adjusting Mechanism Portion

The shell portion 36 further comprises a lower cylindrical hole 44 defining an inwardly extending cylindrical wall 45 having an inner annular edge formed with three 60° spaced apart pairs of diametrically opposite notches such as 46.

A tension-adjusting cam 47 is disposed in the cylindrical hole 44 and is rotatable about its geometrical axis. Cam 47 comprises a circular flat wall 48 and an outer cylindrical wall 89 inwardly extending from the periphery of the circular flat wall 48 and having an annular edge surface formed with a pair of diametrically opposite and outwardly radially extending lugs 49. Cam 47 finally comprises a central inner tube 50 coaxial with the cylindrical wall 89 and inwardly extending from the flat wall 48.

When the diametrically opposite lugs 49 are disposed in a first pair of diametrically opposite notches 46 as shown in FIG. 2, the cam is locked in a first angular position. The point of contact with the distal end section of the blade 30a,30b is therefore a point of the outer tubular surface of the tube 50 when the tension-adjusting cam 47 is locked in the first angular position. This corresponds to the larger extent of spreading apart of the earpieces 11a and 11b before the blades 30a,30b deform and produce a spring action on these earpieces 11a and 11b.

Figure 4:
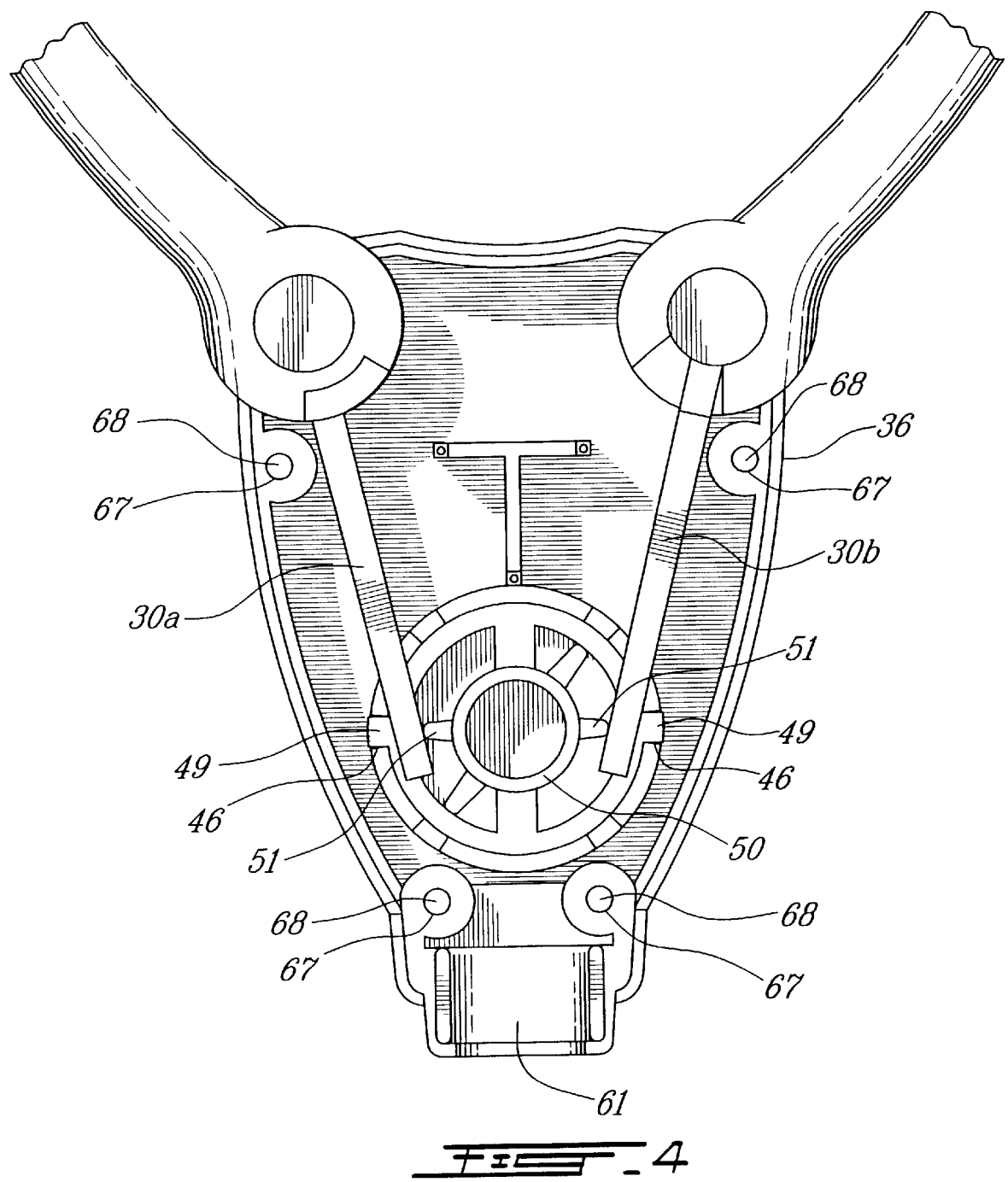
FIG. 4 is a second inner elevation view of the rear shell portion of the neckpiece of the headset of FIG. 1, showing the tension-adjusting cam in a second angular position.

When the diametrically opposite lugs 49 are disposed in a second pair of diametrically opposite notches 46 as illustrated in FIG. 4, the cam is locked in a second angular position. The blades 30a and 30b then rest on respective, diametrically opposite, axial and radial fins 51 of intermediate height formed on the outer tubular surface of the tube 50. The points of contact with the distal end sections of the blade 30a and 30b are therefore the free axial edge surfaces of the fins 51 when the tension-adjusting cam 47 is locked in the second angular position. This corresponds to an intermediate extent of spreading apart of the earpieces 11a and 11b before the blades 30a and 30b deform and produce a spring action on the earpieces 11a and 11b.

Figure 5:
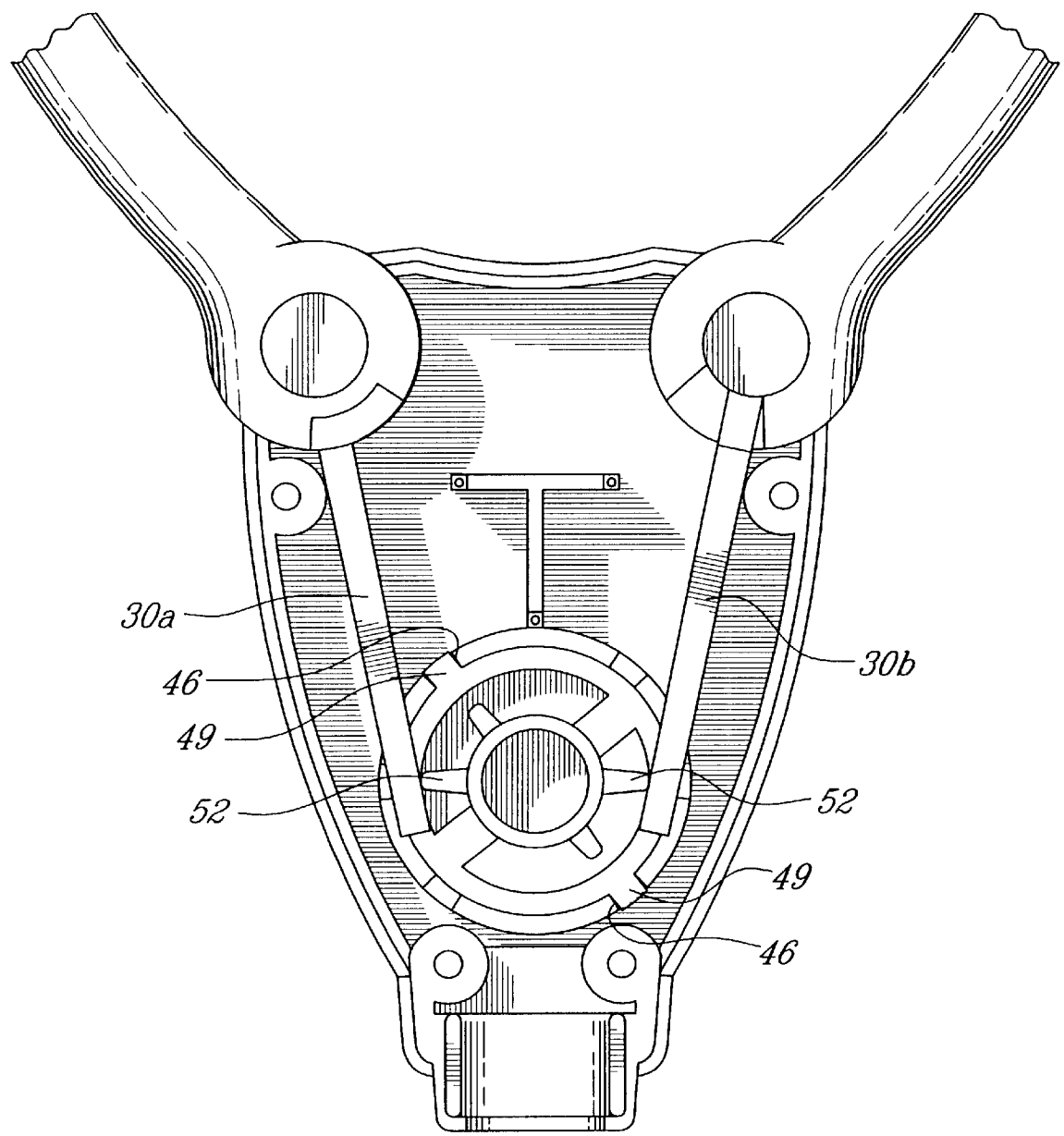
FIG. 5 is a third inner elevation view of the rear shell portion of the neckpiece of the headset of FIG. 1, showing the tension-adjusting cam in a third angular position.

When the diametrically opposite lugs 49 are disposed in a third pair of diametrically opposite notches 46 as illustrated in FIG. 5, the cam 47 is locked in a third angular position. The blades 30a and 30b then rest on respective, diametrically opposite, axial and radial fins 52 of larger height formed on the outer tubular surface of the tube 50. The points of contact with the distal end sections of the blade 30a and 30b are therefore the free axial edge surfaces of the fins 52 when the tension-adjusting cam 47 is locked in the second angular position. This corresponds to an intermediate extent of spreading apart of the earpieces 11a and 11b before the blades 30a and 30b deform and produce a spring action on the earpieces 11a and 11b.

The shell portion 36 further comprises pegs 54 to receive a printed circuit board 53. Of course, the printed circuit board 53 comprises corresponding notches and/or holes such as 55 to receive the pegs 54. The electric wires from hole 38a and 38b can be connected to this printed circuit board 53.

The shell portion 35 comprises holes 62 and 63 for receiving push-buttons 64 and 65, respectively. Push-buttons 62 and 63 operate corresponding switches such as 66 mounted on the printed circuit board.

The headset 10 further comprises a T-shaped anchor 56 formed of a transversal section 57 and a vertical tube 58 perpendicular to section 57. The tube 58 fits in a bottom opening of the shell 35,36. This bottom opening is formed by semi-cylindrical opening portion 60 (FIG. 3) of shell portion 35 and semi-cylindrical opening portion 61 (FIGS. 1 and 4) of shell portion 36. Regarding the section 57, it is shaped to fit inside the shell portions 35 and 36 just above the bottom opening 60,61. Finally, wires from the printed circuit board 53 can run toward the exterior through a hole 59 in the transversal section 57 and then through the tube 58. Just a word to mention that the outer surface of the tube 58 is structured to connect to a biological or other sound sensor (not shown).

Figure 3:
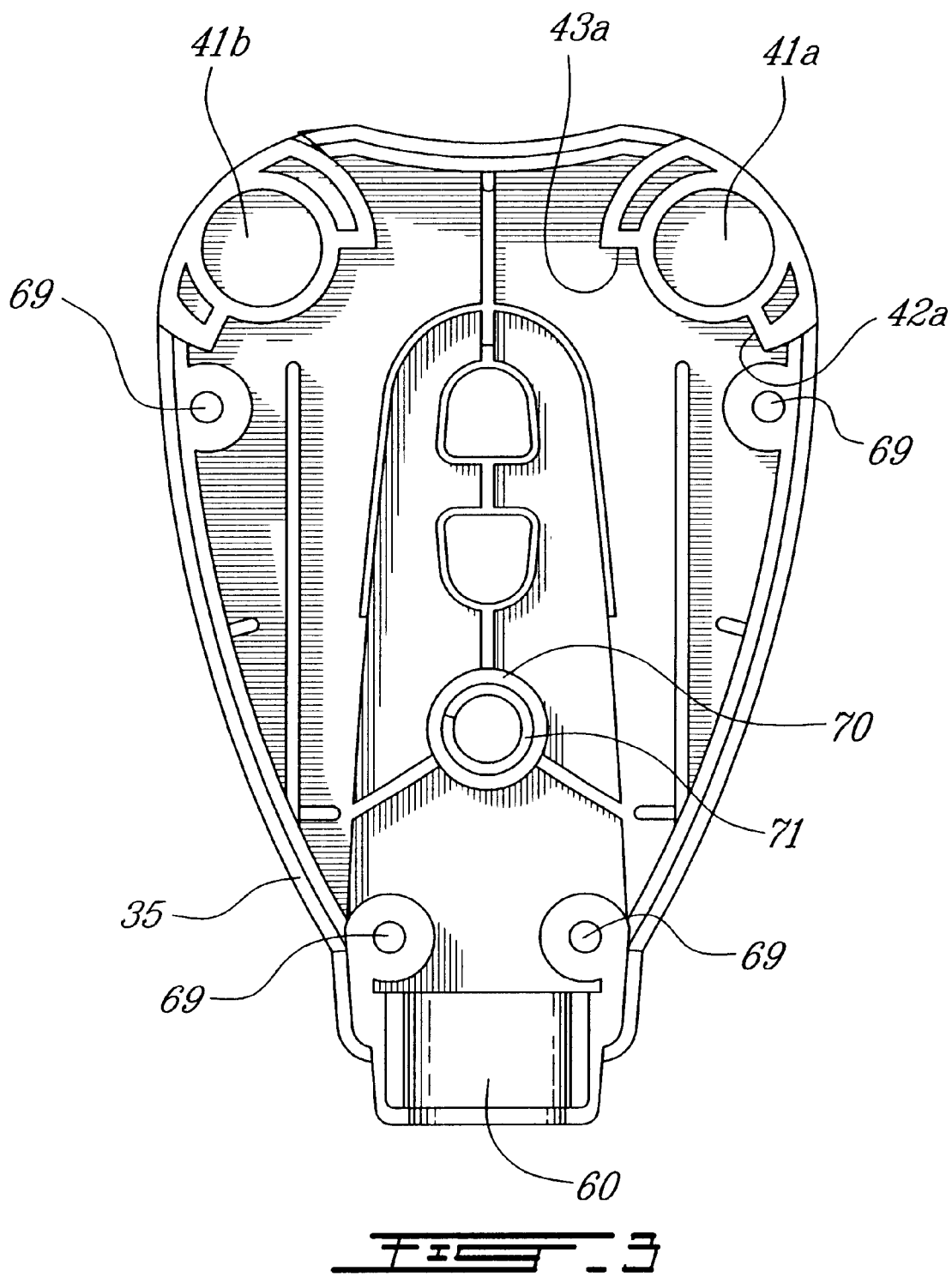
FIG. 3 is an inner elevation view of a front shell portion of the neckpiece of the headset of FIG. 1.

Referring to FIG. 1, the shell portion 35 comprises four holes 67 for receiving four screws 68. Referring to FIG. 3, the shell portion 35 comprises four threaded holes 69 in which the four screws 68 are screwed upon assembling the shell portions 35 and 36 together.

Finally, the shell portion 35 comprises, as shown in FIG. 3, an inwardly extending tube 70 in which a coil spring 71 is installed. When the shell portions 35 and 36 are assembled together, the tube 70 is inserted in tube 50 through a circular hole 73 in the printed circuit board 53, whereby the coil spring extends in both tubes 50 and 70 to push and hold (spring bias) the lugs 49 in one pair of notches 46 and therefore the cam 47 in position in the cylindrical hole 44. To rotate the cam 47 and displace the diametrically opposite lugs 49 from one pair of diametrically opposite notches 46 to the other, one has only to push from the outside the cam 47 until the lugs 49 are withdrawn form the notches 46 and, then, rotate cam 47 clockwise or counterclockwise about its axis until the pair or diametrically opposite lugs 49 can be released to engage the desired pair of diametrically opposite notches 46. The outside face of the circular flat wall 48 can be grooved along a diameter in the same manner as the head of a screw. A coin can then be used in cooperation with this groove (not shown) to facilitate this operation.

To assemble the neckpiece 34, the following operations are performed:

Cam 47 is positioned in cylindrical hole 44 from the inside of the shell half 36 with the pair of diametrically opposite lugs 49 inserted in one of the pair of diametrically opposite notches 46;

The pivot pin 31a is disposed in pivot tube 24a, with the blade 30a and lateral extension 32a in the slot 28a and with the blade 30a lying on the same side of the tube 50 as blind hole 40a;

The corresponding end of pivot pin 31a is positioned in blind hole 40a;

The pivot pin 31b is disposed in pivot tube 24b, with the blade 30b and lateral extension 32b in the slot 28b and with the blade 30a lying on the same side of tube 50 as blind hole 40b;

The corresponding end of pivot pin 31b is positioned in blind hole 40b;

The tube 58 of anchor 56 is placed in semicircular opening portion 61 with one end of the transversal section 57 fitted inside the shell portion 36 above this opening portion 61;

The notches and/or holes 55 of the printed circuit board 53 are engaged with the pegs 54 of the shell portion 36 to thereby mount this printed circuit board 53 in the shell portion 36;

The push-buttons 64 and 65 are placed in the holes 62 and 63, respectively;

One end of the spring 71 is placed in the tube 70;

The shell portion 35 is placed on the shell portion 36 with:
  The free end of the coil spring 71 and the tube 70 of the shell portion 35 inserted in tube 50 of the cam 47;
  The corresponding end of pivot pin 31a positioned in blind hole 41a;
  The corresponding end of pivot pin 31b positioned in blind hole 41b;
  The tube 58 of anchor 56 placed in semicircular opening portion 60, and the corresponding end of the transversal section 57 fitted inside the shell portion 35 above this opening portion 60;
  The push-buttons 64 and 65 above the switches 66; and Finally, the four (4) screws 68 are placed in the four (4) respective holes 67 and, then, screwed in the four (4) respective threaded holes 69.

In operation, restricted free pivotal movement of the pivot tube 24a about the pivot pin 31a, and restricted free pivotal movement of the pivot tube 24a about the pivot pin 31b, restricted pivotal movement of the pivot tube 24a about the neckpiece 34 due to the abutment action of the semicircular lug 26a and surface 42a, restricted pivotal movement of the pivot tube 24b about the neckpiece 34 due to the abutment action of the semicircular lug 26b and surface 42b allow the earpieces 11a and 11b to freely move about the neckpiece 34 about a given, relatively small angle.

Spring Mechanism Portion

When the diametrically opposite lugs 49 of the cam 47 are disposed in the first pair of diametrically opposite notches 46 as shown in FIG. 2, spreading apart of the earpieces 11a and 11b will cause the distal end sections of the resilient blades 30a and 30b to rest on the outer face of the tube 50. The earpieces are then separated by a larger angular spacing. From this larger angular spacing, further spreading apart of the earpieces 11a and 11b will bend the blades 30a and 30b to produce a tension on these earpieces 11a and 11b.

When the diametrically opposite lugs 49 of the cam 47 are disposed in the second pair of diametrically opposite notches 46 as shown in FIG. 4, spreading apart of the earpieces 11a and 11b will cause the distal end sections of the blades 30a and 30b to rest on the free axial edge surface of the respective, diametrically opposite, axial and radial radial fins 51 of intermediate height. The earpieces 11a and 11b are then separated by an intermediate angular spacing. From this intermediate angular spacing, further spreading apart of the earpieces 11a and 11b will bend the blades 30a and 30b to produce a tension on these earpieces 11a and 11b.

When the diametrically opposite lugs 49 of the cam 47 are disposed in the third pair of diametrically opposite notches 46 as shown in FIG. 5, spreading apart of the earpieces 11a and 11b will cause the distal end sections of the blades 30a and 30b to rest on the free axial edge surfaces of the respective, diametrically opposite, axial and radial fins 52 of larger height. The earpieces 11a and 11b are then separated by a smaller angular spacing. From this smaller angular spacing, further spreading apart of the earpieces 11a and 11b will bend the blades 30a and 30b and will produce a tension on these earpieces 11a and 11b.

Accordingly, rotation of the cam 47 about its axis to displace the diametrically opposite lugs 49 from one pair of diametrically opposite notches 46 to the other, will change the angular spacing between the earpieces 11a and 11b allowed prior tension is applied to these earpieces. The user can thereby adjust the angular position of the button 47 in accordance with his requirements, needs and/or preferences.

Although the present invention has been described hereinabove by way of a preferred embodiment thereof, this embodiment can be modified at will, within the scope of the appended claims, without departing from the spirit and nature of the subject invention.

The embodiments of the invention in which an exclusive property or privilege is claimed are defined as follows:

1. A tension-adjusting mechanism for an elongated stethoscope earpiece having a proximal end, comprising:
  a stethoscope neckpiece;
  a pivot mechanism portion interposed between the proximal end of the earpiece and the neckpiece, and defining a pivot axis about which the earpiece pivots relative to the neckpiece;
  a spring mechanism portion interposed between the proximal end of the earpiece and the neckpiece, said spring mechanism portion comprising a spring member which deforms upon pivoting of the earpiece about the neckpiece in an outward direction, wherein deformation of the spring member produces a tension on the earpiece opposing to further pivoting of the earpiece in the outward direction; and
  a tension-adjusting mechanism portion interposed between the spring member and the neckpiece and defining a plurality of interchangeable point of contacts with the spring member, said points of contacts with the spring member having different positions relative to the neckpiece.

2. A tension-adjusting mechanism as defined in claim 1, wherein the neckpiece comprises a hollow shell formed with an opening for the proximal end of the earpiece.

3. A tension-adjusting mechanism as defined in claim 1, wherein the pivot mechanism portion comprises abutment surfaces restricting, by abutment, free pivotal movement of the earpiece about the neckpiece within given limits.

4. A tension-adjusting mechanism as defined in claim 1, wherein the pivot mechanism portion comprises a pivot pin pivotally mounted on the neckpiece, and a pivot tube pivotally mounted on the pivot pin and connected to the proximal end of the earpiece.

5. A tension-adjusting mechanism as defined in claim 4, wherein the spring member comprises a resilient blade having one end formed with said pivot pin.

6. A tension-adjusting mechanism as defined in claim 5, wherein the resilient blade and the pivot pin are made of a single piece of plastic material.

7. A tension-adjusting mechanism as defined in claim 4, wherein the earpiece and the pivot tube are made of a single piece of plastic material.

8. A tension-adjusting mechanism as defined in claim 5, wherein:
  the pivot tube has an open, axial slot through which the resilient blade extends when the pivot pin is inserted in said pivot tube;

the resilient blade has a thickness; and the slot has a width larger than the thickness of the blade to allow pivotal movement of the pivot tube about the pivot pin within predetermined limits.

9. A tension-adjusting mechanism as defined in claim 4, wherein:

the pivot tube has an annular end face provided with a lug;

the neckpiece has a pair of abutment surfaces situated on opposite sides of the lug; and the lug abuts on either abutment surface to restrict pivotal movement of the pivot tube about the neckpiece within predetermined limits.

10. A tension-adjusting mechanism as defined in claim 1, wherein:

the spring member comprises a resilient blade having a proximal end connected to the proximal end of the earpiece, and a distal end section opposite to the proximal end;

the tension-adjusting mechanism portion comprises a tension-adjusting cam having a geometrical axis, rotatable about said geometrical axis and selectively lockable in either first, second and third angular positions;

the tension-adjusting cam comprises an axial member having an outer tubular surface and a first point of contact with the distal end section of the resilient blade formed by said outer tubular surface when the tension-adjusting cam is locked in the first angular position;

the axial member of the tension-adjusting cam comprises, on said outer tubular surface, a first axial and radial fin of intermediate height having a free axial edge surface, and a second point of contact with the distal end section of the resilient blade formed by said free axial edge surface of the first fin when the tension-adjusting cam is locked in the second angular position; and the axial member of the tension-adjusting cam comprises, on said outer tubular surface, a second axial and radial fin of larger height with a free axial edge surface, and a third point of contact with the distal end section of the resilient blade formed by said free axial edge surface of the second fin when the tension-adjusting cam is locked in the third angular position.

11. A tension-adjusting mechanism as defined in claim 10, wherein:

the neckpiece comprises a hole with peripheral notches; and the tension-adjusting cam comprises lugs engaging the peripheral notches of the hole in the neckpiece to lock the tension-adjusting cam in either the first, second and third angular positions.

12. A headset for electronic stethoscope, comprising:

first and second elongated stethoscope earpieces each having a proximal end; and a tension-adjusting mechanism as recited in claim 1 for each elongated stethoscope earpiece.

13. A headset as recited in claim 12, wherein the stethoscope neckpiece is common to both the first and second elongated stethoscope earpieces.

14. A headset as recited in claim 12, wherein the neckpiece comprises a hollow shell formed with openings for the proximate ends of the earpieces.

15. A headset as recited in claim 14, wherein the hollow shell comprises a front shell portion and a rear shell portion assembled together to form said hollow shell.

16. A headset as recited in claim 12, wherein, for each earpiece, the pivot mechanism portion comprises abutment surfaces restricting, by abutment, free pivotal movement of the earpiece about the neckpiece within given limits.

17. A headset as recited in claim 12, wherein, for each earpiece, the pivot mechanism portion comprises a pivot pin pivotally mounted on the neckpiece, and a pivot tube pivotally mounted on the pivot pin and connected to the proximate end of the earpiece.

18. A headset as defined in claim 17, wherein, for each earpiece, the spring member comprises a resilient blade having one end formed with said pivot pin.

19. A headset as recited in claim 18, wherein, for each earpiece:

the pivot tube has an open, axial slot through which the resilient blade extends when the pivot pin is inserted in said pivot tube;

the resilient blade has a thickness; and the slot has a width larger than the thickness of the resilient blade to allow pivotal movement of the pivot tube about the pivot pin within predetermined limits.

20. A headset as recited in claim 17, wherein, for each earpiece:

the pivot tube has an annular end face provided with a lug;

the neckpiece has a pair of abutment surfaces situated on opposite sides of the lug; and the lug abuts on either abutment surface to restrict pivotal movement of the pivot tube about the neckpiece within predetermined limits.

21. A headset as recited in claim 18, wherein:

the resilient blade associated to the first earpiece has a first distal end section opposite to the pivot pin;

the resilient blade associated to the second earpiece has a second distal end section opposite to the pivot pin;

the tension-adjusting mechanism portion associated to both the first and second earpieces comprises a tension-adjusting cam having a geometrical axis, rotatable about said geometrical axis and lockable in either first, second and third angular positions;

the tension-adjusting cam comprises an axial member having an outer tubular surface and two first points of contact with the first and second distal end sections, respectively, formed by two points of said outer tubular surface, respectively, when the tension-adjusting cam is locked in the first angular position;

the axial member of the tension-adjusting cam comprises, on said outer tubular surface, first and second diametrically opposite, axial and radial fins of intermediate height having respective first and second free axial edge surfaces, and two second points of contact with the first and second distal end sections, respectively, formed by said first and second free axial edge surfaces of the first fin, respectively, when the tension-adjusting cam is locked in the second angular position; and the axial member of the tension-adjusting cam comprises, on said outer tubular surface, third and fourth geometrically opposite, axial and radial fins of larger height with third and fourth free axial edge surfaces, respectively, and two third points of contact with the first and second distal end sections, respectively, formed by said third and fourth free axial edge surfaces of the second fin, respectively, when the tension-adjusting cam is locked in the third angular position.

22. A headset as recited in claim 11, wherein:

the neckpiece comprises a hole with peripheral notches; and the tension-adjusting cam comprises lugs engaging the peripheral notches of the hole in the neckpiece to lock the tension-adjusting cam in either the first, second and third angular positions.

23. A headset as recited in claim 22, wherein the tension-adjusting mechanism associated to both the first and second earpieces comprises:

a spring element interposed between the neckpiece and the tension-adjusting cam and spring biasing the lugs of said tension-adjusting cam in the notches of the hole in the neckpiece;

whereby, to be rotated, the tension-adjusting cam is moved against the spring-biasing force produced by the spring element to disengage the lugs from the notches and is rotated and then released to engage the lugs with other notches.

* * * * *